(12) United States Patent
Chartrel

(10) Patent No.: US 10,779,995 B2
(45) Date of Patent: Sep. 22, 2020

(54) PROCESS FOR DOSING SUPER ABSORBENT PARTICLES

(71) Applicants: BOSTIK INC., Wauwatosa, WI (US); BASF SE, Ludwigshafen (DE)

(72) Inventor: Jean Francois Chartrel, Cuts (FR)

(73) Assignees: BASF SE, Ludwigshafen (DE); BOSTIK INC., Wauwatosa, WI (US)

( * ) Notice: Subject to any disclaimer, the term of this patent is extended or adjusted under 35 U.S.C. 154(b) by 344 days.

(21) Appl. No.: 14/654,219

(22) PCT Filed: Dec. 20, 2013

(86) PCT No.: PCT/EP2013/077866
§ 371 (c)(1),
(2) Date: Jun. 19, 2015

(87) PCT Pub. No.: WO2014/096438
PCT Pub. Date: Jun. 26, 2014

(65) Prior Publication Data
US 2015/0313764 A1 Nov. 5, 2015

Related U.S. Application Data

(60) Provisional application No. 61/740,688, filed on Dec. 21, 2012.

(30) Foreign Application Priority Data

Dec. 21, 2012 (EP) ..................................... 12199197

(51) Int. Cl.
*A61F 13/15* (2006.01)
*B32B 37/18* (2006.01)
*A61F 13/532* (2006.01)

(52) U.S. Cl.
CPC .. *A61F 13/15658* (2013.01); *A61F 13/15642* (2013.01); *A61F 13/5323* (2013.01);
(Continued)

(58) Field of Classification Search
CPC ......... A61F 13/15; A61F 13/532; B32B 37/01
See application file for complete search history.

(56) References Cited

U.S. PATENT DOCUMENTS 5,156,902 A * 10/1992 Pieper ............... A61F 13/15577
428/206
6,033,199 A 3/2000 Vonderhaar et al.
(Continued)

FOREIGN PATENT DOCUMENTS

CN 102770098 A 11/2012
EP 2540267 B1 2/2015
(Continued)

OTHER PUBLICATIONS

Haeberle, et. al "Centrifugal Micromixery" Chemical Engineering & Technology, 2005 (see attached).*
(Continued)

*Primary Examiner* — Andrew J Mensh
(74) *Attorney, Agent, or Firm* — Millen, White, Zelano & Branigan, PC; Ryan Pool (57) ABSTRACT

The present invention is directed to a novel process for dosing super absorbent polymer particles into a plurality of particles flows, comprising the steps of: (i) providing super absorbent polymer particles; (ii) imparting a rotation to said particles; and (iii) collecting separate flows of particles, wherein the step (ii) is performed with a rotating mobile (11) provided into a housing (12).

Use for manufacturing absorbent article and article thus obtained.

11 Claims, 3 Drawing Sheets

(52) U.S. Cl.
CPC ...... *B32B 37/18* (2013.01); *B32B 2307/7265* (2013.01); *B32B 2555/02* (2013.01); *Y10T 137/0318* (2015.04); *Y10T 137/6851* (2015.04); *Y10T 156/10* (2015.01)

(56) References Cited

U.S. PATENT DOCUMENTS

| | | |
|---|---|---|
| 2013/0025792 A1 | 1/2013 | Ninomiya |
| 2014/0087360 A1* | 3/2014 | Woodside ............ G01N 33/491 435/2 |

FOREIGN PATENT DOCUMENTS

| | | |
|---|---|---|
| JP | 2006-263074 A | 10/2006 |
| JP | 2011177299 A | 9/2011 |
| SU | 1703181 A1 * | 1/1992 |

OTHER PUBLICATIONS

International Search Report dated Feb. 24, 2014 issued in corresponding PCT/EP2013/077866 application (pp. 1-3).
English Translation Abstract of JP 2006-263074 A published Oct. 5, 2006.
Translated Exam Report in corresponding CN 201380073621.6 dated Sep. 19, 2018 (pp. 1-22).
Translated Notification of reasons for refusal in corresponding JP 2015-548670 dated Nov. 28, 2017 (pp. 1-8).

* cited by examiner

PROCESS FOR DOSING SUPER ABSORBENT PARTICLES

FIELD OF THE INVENTION

The present invention is directed to a novel process for dosing super absorbent polymer particles into a plurality of particles flows, said flows being substantially of similar flow rates. The invention also provides for a process for manufacturing absorbent articles, where the articles comprise super absorbent polymer particles.

BACKGROUND OF THE INVENTION

Absorbent articles are known and commonly used in personal care absorbent products such as diapers, training pants, sanitary napkins, incontinence garments, bandages and the like. The invention also relates to a process for making said article.

Nowadays, the absorbing element in the article is comprised of high absorbency materials such as superabsorbents (Super Absorbent Polymers—SAP—), which form the diaper's absorbent core.

While the SAP has many advantages, it is also difficult to dose, given the fact that SAP is available as a powder. The problem is not acute for uniform layers dispensing devices, but becomes very relevant when SAP patterns are required.

For distributing SAP particles according to different flows, it is possible to use specific dosing devices dedicated to each specific flow (and associated pattern). Yet, this implies high costs and maintenance problems. Also, this may not be possible in certain circumstances, due to the volume needed to install all dosing devices. Known systems for forming different flows typically comprise vibrating belt and separating devices at the extremity of the belt. Yet, these systems suffer from a great variability in the flow rates and PSD (Particle Size Distribution) of each flow.

SUMMARY OF THE INVENTION

The invention thus provides a process for dosing super absorbent polymer particles into a plurality of particles flows, comprising the steps of:
(i) providing super absorbent polymer particles;
(ii) imparting a rotation to said particles, said step (ii) being performed with a rotating mobile (11) provided into a housing (12); and
(iii) collecting separate flows of particles.

The invention also provides for a dosing apparatus, notably for implementing the process according to the invention, comprising (i) a housing (12), and a rotating mobile (11) provided into said housing (12).

According to one embodiment, the gap between the mobile (11) and the housing (12) is about 5 mm to 20 mm, preferably 10 mm to 15 mm.

According to one embodiment, the rotating mobile (11) has a J shape.

According to one embodiment, the J shape of the rotating mobile (11) is derived from a parabola having its axis on the radius of said mobile, preferably at a distance of 65% to 90%, preferably 70% to 85%, more preferably from 75% to 80% from the center.

According to one embodiment, the J shape of the rotating mobile (11) comprises an angle formed by the J curve at the periphery of the mobile with the equator plane from 5° to 30°, preferably from 7° to 25°, more preferably from 10° to 22°.

According to one embodiment, the mobile (11) has a diameter from 50 to 250 mm, preferably from 100 to 200, more preferably about 135 mm to 175 mm.

According to one embodiment, the housing (12) has an inner diameter of about 60 to 300 mm, preferably from 110 to 215 mm, more preferably from 160 mm to 200 mm.

According to one embodiment, the rotating speed of said mobile (11) is from 100 to 1000 rpm, preferably from 200 to 800 rpm, more preferably from 300 to 500 rpm.

According to one embodiment, the rotating speed of said mobile (11) is such that the particles will operate at least one revolution.

According to one embodiment, the rotating speed of said mobile (11) is such that the particles will have a peripheral speed from 0.5 m/s to 8 m/s, preferably from 2 m/s to 4 m/s.

According to one embodiment, the step (ii) comprises the step of forming a curtain (13) of particles.

According to one embodiment, the step (iii) of collecting the separate flows of particles comprises collecting particles into equally distributed apertures (14a, 14b, 14c, 14d).

According to one embodiment, the step (i) of providing the particles comprises supplying the particles gravitationally or using a screw device.

According to one embodiment, the step of supplying the particles is carried out substantially along the axis of the rotation of step (ii).

According to one embodiment, the step (i) of providing the particles comprises supplying the particles through a circular nozzle (15) placed around the axis of rotation.

According to one embodiment, the circular nozzle (15) defines an aperture which is annular in shape and has a lumen from 5 mm to 20 mm, preferably from 7 mm to 12 mm, more preferably from 10 mm to 15 mm.

According to one embodiment, the circular nozzle (15) is placed at a distance of 2 mm to 17 mm, preferably about 5 to 12 mm above the point of junction between the shape and the axis of the mobile (11).

According to one embodiment, the circular nozzle (15) comprises an inner shape of conical geometry, with an angle relative to the vertical from 45° to 75°, preferably from 50° to 70°.

According to one embodiment, the housing (12) comprises a bottom part having an inner shape with an angle relative to the vertical from 70° to 85°, preferably from 75° to 80°.

According to one embodiment, the step (iii) of collecting is for collecting a number of separate flows of particles from 2 to 8, preferably 4 or 6.

The invention further provides a process for manufacturing an absorbent article (1) comprising super absorbent polymer particles, comprising dosing the particles according to the process as recalled above and subject of the present invention.

According to one embodiment, the process is for manufacturing an absorbent article (1), said article comprising:
a first sheet layer (2) presenting an array of absorbent receiving pockets (4, 4a);
masses (6) of superabsorbent material, which masses are placed in said absorbent receiving pockets (4, 4a);
a second sheet layer (7) placed on top of the first layer;
said process comprising the steps of
providing a first sheet layer (2);
providing an array of pockets (4, 4a) into said first sheet layer;
providing SAP particulate material (6) according to the process for dosing of the invention;

providing a second sheet layer (7) material and affixing it for sandwiching with the first sheet layer;

finishing the absorbent article.

According to one embodiment, the process further comprises the step of converting said absorbent article (1) into a diaper, training pant, sanitary napkin, incontinence garment or bandage.

The invention also provides an absorbent article obtainable by the process of the invention as recalled above, wherein the particle size distribution (PSD) of the fluid-absorbent polymer particles in one pocket varies from the PSD of the fluid-absorbent polymer particles in any other pocket by not more than 15%.

The invention thus allows the formation of flows of SAP particles having substantially similar flow rates and similar PSDs. This allows avoiding recourse to a multiplicity of dosing apparatuses, and thus allows gains for costs and for maintenance.

DESCRIPTION OF EMBODIMENTS OF THE INVENTION

The invention is now disclosed in more details below, in a non-limiting manner.

Figure 1:
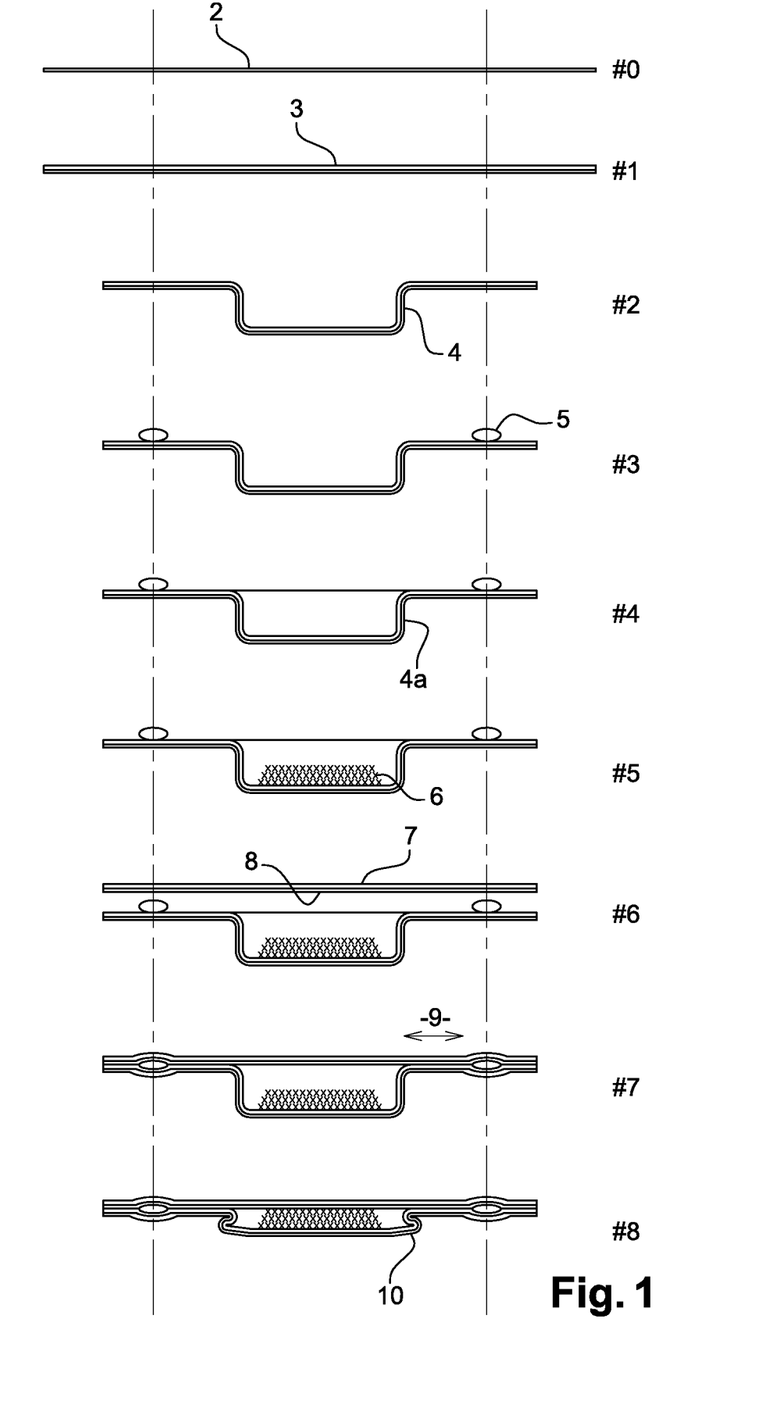
FIG. 1 represents the formation of the absorbent article of the invention.

Reference is made to FIG. 1 which discloses the formation of the absorbent article of the invention according to one embodiment.

In an initial step, a first sheet layer (2) is provided. This first layer will serve as the bottom layer. It may be impervious to liquids, but this is not necessary in case of the presence of an impervious backsheet in the diaper for example.

This layer then receives a layer of adhesive (3). This adhesive is typically a hot-melt, as will be disclosed in more details below. The adhesive may be present on the entire surface or only at the vicinity of the sealed area. It is preferred that the adhesive be present on the entire surface (in a continuous or discontinuous manner). With this embodiment, the adhesive will receive the SAP and will adhere to it so that most of the SAP will be caused to adhere to the surface of the sheet layer. This will improve the SAP position and further prevent SAP from slipping within the disposable diaper.

The sheet layer (2) with the adhesive layer (3) is then formed into the desired shape. Different techniques may be used to form the shape of the pocket (4, 4a), as is known in the art. In the embodiment that is disclosed, the step is disclosed in relation with the machine direction, forming bands, a specific step with respect to the transverse direction is applied later on.

Figure 2:
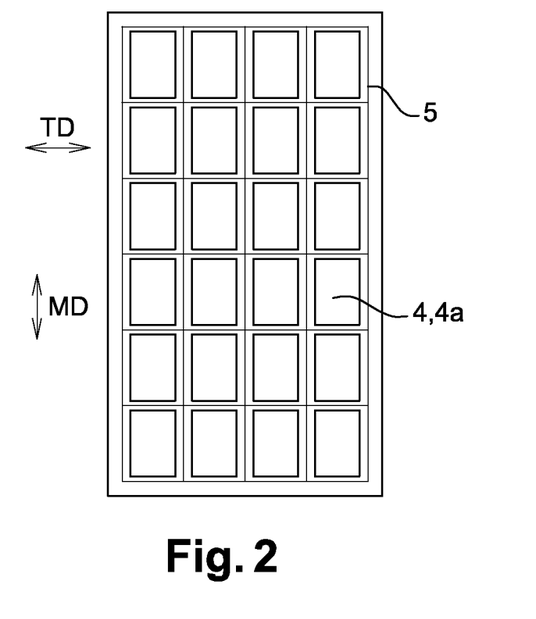
FIG. 2 represents a schematic illustration of the top view of an absorbent article according to the invention.

Adhesive beads (5) (also known as adhesive ropes) are then applied at a location between the pockets (4, 4a) previously formed, as illustrated in FIG. 2, which is a top view of an adsorbent core with pockets in rectangular shape and beads in the machine direction (MD) and transverse direction (TD). Standard techniques are used.

The beads ensure structural strength by keeping the sheet layers bonded during use.

The step of forming the pockets in the transverse direction is then performed; this step is optional but preferred. The step of adhesive beads deposition can be performed before or after the step of forming the transverse direction forms for the pockets. It may also be performed at about the same time.

The pockets thus formed can have various shapes and forms. For example, the pockets can be rectangular or square in shape with varying lengths of their respective sides. For example the length may vary from 10 mm×10 mm to 10 mm×80 mm, including 20 mm×20 mm to 20 mm×60 mm or 20 mm×20 mm to 40 mm×40 mm or 20 mm×40 mm with varying shapes, in any direction. The depth of the final pocket depends e. g. on the mass of SAP material to be filled in. For example for baby diapers a depth from 1 mm to 5 mm (once finally formed, i.e. calendered) may be preferred. Any other desired geometric forms and patterns are conceivable. Particular preference is also given to the application of one or more continuous strips in machine running direction, the strips running parallel to one another.

Thus a longitudinal type pocket is possible; in this case the pocket will be elongated, e.g. from 10-80 mm×100-400 mm.

The SAP is then placed in the thus-formed pockets, using an appropriate dosing device, using the device that is as disclosed below.

The second sheet layer (7) receives first an adhesive layer (8). The second sheet layer is typically water-permeable so as to allow the fluids to penetrate through and reach the SAP. This second sheet will typically serve as the top layer. The adhesive layer will not be complete or will be porous, so as to allow transfer of fluid through the sheet layer. The adhesive layer (8) is optional and may be omitted.

The second sheet layer (7) with the adhesive layer (8) is then affixed onto the first sheet layer (2) with the pockets (4, 4a) containing the SAP (6) and bearing the beads (5). This is done in an area (9) in the vicinity of the beads (5).

Calendering is then performed on the sandwich thus formed (where pleats (10) are formed), ensuring the bonding of the two sheet layers.

For example, a pressure sensitive adhesive is applied directly on the bottom layer of the assembly (a nonwoven). The same adhesive is also applied directly on the top layer of the assembly (a nonwoven. The top layer was mounted on the bottom layer and pressed using a pressure roll. In another embodiment, the previous assembly was reiterated but inserting between the adhesive-coated top and bottom layers, a bead of adhesive. The same method is used to create the assembly, making sure that the adhesive bead is placed in the middle of the pressed laminate.

SAP is maintained in a very efficient way in the pockets formed in the invention, being prevented from slipping and/or aggregating at one place in the article.

The steps for manufacturing the article of the invention and the various elements thereof are disclosed in more details below.

The SAP that is used in the invention is any product that is able to absorb water to a significant amount. A typical SAP will absorb water from 10 to 50 times its dry volume, typically from 20 to 40 times (the ratio can be higher if expressed in terms of weight ratios). For example, 15 g of SAP may retain 400 cc of fluid (tested as 4 successive wettings, 4×100 cc). BASF is exemplary of a company supplying SAP. SAP is generally available as a powder, with varying particle size (e.g. more than 60% of the particles flow through a mesh from 100 μm to 850 μm). Typically SAPs are (meth)acrylic polymer, especially alkali metal salts of polyacrylic acids. Core-shell polymers can be used, where the inner is absorbing and the outer is an osmotic membrane. SAPs are well known for the skilled man.

The production of fluid-absorbing polymer particles (Super Absorbent Polymers—SAP—) is likewise described in the monograph "Modern Superabsorbent Polymer Technology", F. L. Buchholz and A. T. Graham, Wiley-VCH, 1998, pages 71 to 103.

The SAP may also be the one disclosed in WO2010/133529, from page 6 line 1 to page 15 line 16, incorporated herein, by reference. The SAP load may vary within broad limits. For example, for a baby diaper, the amount of SAP usually used is from 8 to 20 g, preferably from 11 to 18 g, more preferably from 12 to 15 g.

The invention also uses sheet layers, one typically as a bottom layer and one typically as a top layer. Typically, both sheets are non-woven. Non-woven can be manufactured using different technologies and one can cite staple non-woven, spunbonded non-woven, spunlaid non-woven, airlaid non-woven, and the like. Bonding can be mechanical (e.g. entanglement), thermal, ultrasonic, chemical, and the like. Non-woven are well-known for the man skilled in the art. The non-woven used can be standard or can be structured, and can also be already embossed if needed.

The non-woven can be pervious to liquids or impervious to liquids. The skilled man will select the fibers to be used to match the requirements. Hydrophilization of fibers is known to render fibers suitable for the manufacture of liquid-pervious non-woven.

Fibers can be customary synthetic or semi-synthetic fibers, such as polyesters, polyolefins and rayon, or customary natural fibers, such as cotton. In the case of nonwoven materials, the fibers can be bonded by binders such as polyacrylates. Preferred materials are polyester, rayon, polyethylene and polypropylene. Examples of liquid-pervious layers are described, for example, in WO 99/57355 A1 and EP 1 023 883 A2.

Examples of liquid-impervious layer are layers consisting typically of hydrophobic polyethylene or polypropylene; other material can be used such as polyester and polyamide.

Multilayer structures are also possible, so as to provide for a specific aspect or feel on one side of the sheet and specific properties on the other side, e.g. with respect to adhesion.

References EP1609448, as well as US2008/0045917 provide for disclosure of such non-wovens.

The top layer will be permeable to liquids, so as to allow the liquid being entrapped by the SAP. A possible non-woven for the top layer will be one with polyethylene or polypropylene fibers having received a hydrophilization treatment, or rayon or any other suitable fibers. The references above contain a disclosure of possible top layers. The surface weight can vary between wide ranges, such as from 5 to 100 g/m$^2$, preferably from 10 to 50 g/m$^2$.

The bottom sheet layer will be impervious to liquids, as is usually the case, but not necessarily. A possible layer is a non-woven layer. A possible non-woven for the bottom layer will be one with polypropylene or polyester fibers, as is well-known for the skilled man. The references above contain a disclosure of possible bottom sheet layers. The surface weight can vary between wide ranges, such as from 5 to 100 g/m$^2$, preferably from 10 to 50 g/m$^2$. The bottom sheet layer will also have a porosity to air that will be controlled. This will assist in forming the pockets and filling in the SAP, as will become more apparent below.

The adhesives used in the invention are known for the skilled man. The first type of adhesive is used for the beads. The adhesive for the beads is typically a hot-melt. It may be typically a PSA (Pressure Sensitive Adhesive). The preferred adhesive is thus a HMPSA. Exemplary HMPSA that may be used for the beads is an SBS-based adhesive with hydrogenated hydrocarbon resins and naphthenic oil. The process for adhesive deposition is known to the skilled man, and the lines can be continuous or broken, preferably continuous. The linear weight is from 0.1 to 5 g/linear meter.

Beads can be present in the machine direction (MD), transverse direction (TD) or both. The beads ensure geometrical stability of the absorbent article. The beads also ensure a draining function. The liquid can migrate within the thickness of the sheet layer esp. the non-woven. At the beads level, the liquid will be guided along the pathways defined by the beads, and draining pathways will then be defined. This ensures a more uniform distribution of the fluid over the entire absorbent article.

Similar adhesives are used for adhesives layers (3) and (8) (if present). The adhesives may not be the same for the top layer and the bottom layer. The adhesive may be deposited using techniques known to the skilled man. The coating can be total or partial (multi lines, multi dots, according to specific patterns, MD, TD, spiral spray, porous coating, foam coating, and the like). The adhesive, if used on the top layer, will be such that fluids will be able to go through the top layer. Hence, the coating for the top layer is usually an open coating. The surface weight will usually be from 5 to 60 g/m2, preferably from 10 to 20 g/m2. Adhesives used with the sheet layers (beads or deposited on the sheet layer) are preferably not hydrosoluble.

Hot melts are preferred, especially Pressure Sensitive Adhesives (PSA, especially HMPSA).

Very generally speaking, and without this being limiting, the hot melt adhesives comprise:

(a). Polymers such as EVA, PE, PP, EEA (ethylene ethyl acrylate) and the thermoplastic elastomers or rubbers which are (block) styrene copolymers such as SIS, SIBS, SEPS, SBS, SEBS, or butadiene-based polymers or, yet again, ethylene-propylene copolymers such as EPR, and Olefin Block Copolymer OBC. A chemical modification such as maleic anhydride modification is possible.

A typical average molar mass in weight MW is between 60 kDa and 400 kDa for the polymer.

They can make up from 10 to 80%, preferably 15 to 40% of the formulation and their purpose is to provide: mechanical strength, flexibility, barrier properties, brilliance and viscosity control.

(b). tackifying resins which can be polar or non-polar resins. Polar resins can be (i) rosins of natural or modified origin, such as for example the rosin extracted from the gum of pinewood, their polymerized, dimerized, dehydrogenated, hydrogenated derivatives or esterified by monoalcools or polyols like glycol, glycerol, pentaerythritol; (ii) terpenic resins generally resulting from the hydrocarbon polymerization terpenic in the presence of catalysts of Friedel-Crafts like the mono-terpene (or pinene), the alpha-methyl styrene, and possibly modified by phenol action. Non-polar resins can be (iii) resins obtained by hydrogenation, polymerization or copolymerization (with an aromatic hydrocarbon) of mixtures of unsaturated aliphatic hydrocarbons resulting from oil cuts; (iv) terpenic resins generally resulting from the terpenic hydrocarbon polymerization in the presence of catalysts of Friedel-Crafts such as for example mono-terpene (or pinene), copolymers containing natural terpenes, for example styrene/terpene, the alpha-methyl styrene/terpene and the vinyl toluene/terpene.

Tackifying resins can be natural (rosin esters, terpene or terpene-phenolic esters), or oil-based, aliphatic or aromatic.

They make typically up from 10 to 80%, preferably 30 to 60%, of the formulation. They increase the hot tack, adherence and control cohesion.

(c). Paraffins and waxes, which can make up from 0 to 20% of the formulation. They play a role in providing barrier, rigidity and hot melt hardness properties.

(d). Plasticizers such as oils which can make up some 0 to 30% of the formulation. They control hot melt flexibility and viscosity.

(e). Anti-oxidants which may make up from 0.2 to 2% of the formulation. They stabilize the components when hot and when cold.

(f). Fillers which may make up part of the formulation when particular properties are desired such as UV-resistance (oxidation resistance), flame proofing, anti-allergy properties, rheology modification, etc.

An hot-melt may have the following composition: 15 to 40% thermoplastic polymer, 30 to 60% tackifying resin, 30% or lower of other constituents: plasticizing oil, anti-oxidation agents, additives etc.

Residual tack can be controlled by adjusting the ingredients and the formulation.

An adhesive may also be used with the SAP. This may assist in reducing the SAP movements. This can be, as disclosed above an HMA, HMPSA. It may also be water based (WB), and for example it can be a WBPSA. The adhesive used together with the SAP can be hydrosoluble. This adhesive can be deposited at the same time the SAP is placed in the formed pockets. This embodiment will allow a tighter holding of the particles or grains of SAP, which is beneficial for the process and/or design.

The absorbent article can be manufactured using various processes known in the art. One may revert for example to the following references: EP-A-1621166 and EP-A-1621167 (to P&G), US2010/0100065 (To Fameccanica), EP724418, EP725613, EP725615 and EP725616 (to Kimberly-Clark), WO2012/048878, WO2012/048879, WO2012/052172, WO2012/052173 (to Vynka and Romanova).

The dosing apparatus of the invention is used to deliver the needed SAP flows into the manufacturing line.

Figure 3:
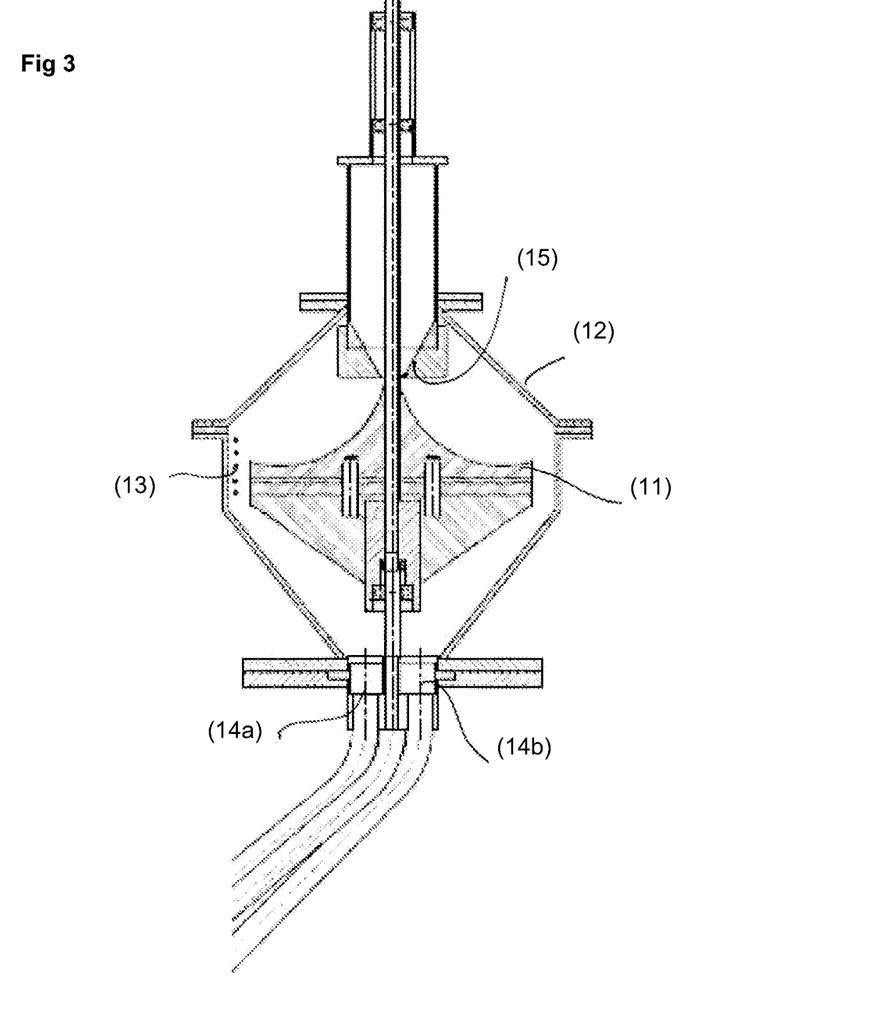
FIG. 3 represents a cut of a dosing apparatus according to the invention.

The dosing apparatus of the invention is disclosed in more details with reference to FIG. 3. In this embodiment, and preferably, the axis of the rotating mobile is vertical.

As a matter of example, and not in a limiting manner, the following parameters and manufacturing details have been found appropriate, for distributing cumulated flow rates of 2 kg/hour to 120 kg/hour.

The mobile (11) has a J shape, and is generally a parabola-shaped mobile (11). The diameter of said mobile can be from 50 to 250 mm, preferably from 100 to 200, typically about 135 mm to 175 mm, and the inner diameter of the housing (12) is about 60 to 300 mm, preferably from 110 to 215 mm, typically from 160 mm to 200 mm.

The gap between the mobile and the housing is about 5 mm to 20 mm, preferably 10 mm to 15 mm.

The height of the mobile, counted from the equator, is generally from 35 to 75 mm, preferably from 40 to 70, typically from 47.5 mm to 62.5 mm.

The J curve typically forms a smooth transition with the axis of the mobile.

The angle formed by the J curve at the periphery of the mobile with the equator plane is generally from 5° to 30°, preferably from 7° to 25°, typically from 10° to 22°.

The J shape of the rotating mobile (11) is preferably derived from a parabola having its axis on the radius of said mobile, at a distance of generally 65% to 90%, preferably 70% to 85%, typically from 75% to 80% from the center.

The main axis diameter is from 5 to 10 mm, typically about 8 mm and will assist in creating an annular shape flow space.

The nozzle (15) for supplying the SAP particles has an annular shape around the axis of the mobile and has a lumen (defined as the gap between the outer of the mobile axis and the inner diameter of the nozzle) which is generally from 5 mm to 20 mm, preferably from 7 mm to 12 mm, typically from 10 mm to 15 mm, for example about 12 mm. The diameter of this part of the dosing device is linked to the flow rate and the value of 12 mm is well adapted to the range of 40 kg/hour to 80 kg/hour.

The nozzle (15) is placed about 2 mm to 17 mm, preferably about 5 to 12 mm, typically about 8 mm above the point of junction between the shape and the axis of the mobile.

The nozzle (15) comprises an inner shape of conical geometry, with an angle relative to the vertical from 45° to 75°, preferably from 50° to 70°, typically about 60°.

Particles are typically supplied gravitationally into the nozzle. It is also possible to supply the particles using a specific device such as a screw. The supply is preferably carried out substantially along the axis of the rotation of the mobile.

The housing (12) comprises a bottom part having an inner shape with an angle relative to the vertical from 70° to 85°, preferably from 75° to 80°, typically about 77°.

The surface of the inner parts of the housing will have a roughness such that the SAP particles will flow on this surface and will not accumulate.

At the very lower part of the device are located apertures (14a, 14b, 14c, 14d) in the form of channels, equally located. Typically there are four apertures or channels, but 2 or 3 is also possible, as well as higher numbers such as 5, 6 or 8. The apertures or channels collect the SAP particles for further distribution in the line thereafter.

The above parameters can be reset and redefined for varying SAP particles, varying flow rates, and generally speaking the desired properties of the flows.

The mobile can thus be defined as fixed along the axis, or it can be displaced along its axis so as to vary the distance from the nozzle. The mobile can have a fixed base, and different forms that can be adapted, so as to be able to vary the shape, and/or the gap between the mobile and the housing. To that extent, shimming plates are provided. The lumen of the nozzle can be adapted to the flow rate, a larger lumen being required for larger flow rates. The different angles of the dosing device can also be adapted.

The parameters are also related by the peripheral speed. For each flow (range of flow), an optimum rotation speed can be defined, related to the diameter of the mobile.

The rotation speed is selected such that, generally, the particles will have a peripheral speed from 0.5 m/s to 8 m/s, preferably from 2 m/s to 4 m/s (it being recalled that the peripheral speed $(m/s)=(rpm/60) \cdot 2 \cdot \pi \cdot (\phi/2)$ with $\phi$ being the diameter of the rotating mobile.).

The dosing device of the invention allows then for the formation of a curtain (13) of particles, where the curtain will be substantially homogeneous. The curtain is obtained typically when the particles operate at least one revolution around the axis of the dosing apparatus, given the rotation of the mobile. Having an homogeneous curtain allows obtaining flows in the below apertures or channels with substantially the same flow rate and substantially the same PSD. Thanks to the rotation and the peripheral speed, the particles will impact the walls of the housing without breaking, thereby maintaining their physical integrity. The dosing apparatus of the invention allows handling fragile SAP particles.

Setting parameters, especially the flow rate and the rotation speed can be set each with respect to the other. The % deviation for a given flow rate is generally a function of the rotation speed, and the % deviation for a given rotation speed is generally a function of the flow rate. Thus, once a flow rate is set, given the required industrial demand, the rotation speed can be varied and the rotation speed is set for the minimum deviation. For example, a value of 400 rpm is well adapted to the flow rate range of 40 kg/hour to 80 kg/hour. The rotation speed of the mobile can vary from 100 to 1000 rpm, preferably from 200 to 800 rpm, more preferably from 300 to 500 rpm.

With the above parameters for the dosing apparatus, it has been possible to provide four flows, with the following repartitions (in %, sum at 100%), for a flow rate of 58 kg/hr and a rotation speed of 400 rpm. Below is a table providing for 4 different runs (1 to 4), with the channels (14*a*, 14*b*, 14*c*, 14*d*) identified:

| Channel | Run 1 kg/h | Run 1 % | Run 2 kg/h | Run 2 % | Run 3 kg/h | Run 3 % | Run 4 kg/h | Run 4 % |
|---|---|---|---|---|---|---|---|---|
| 4a | 14.12 | 24.35 | 13.41 | 23.11 | 13.83 | 23.80 | 12.91 | 22.22 |
| 4b | 15.08 | 26.00 | 15.22 | 26.23 | 15.31 | 26.35 | 14.76 | 25.40 |
| 4c | 14.51 | 25.02 | 15.18 | 26.16 | 15.11 | 26.01 | 15.11 | 26.01 |
| 4d | 14.28 | 24.62 | 14.22 | 24.50 | 13.85 | 23.84 | 15.32 | 26.37 |
| Total | 57.99 | 100.00 | 58.03 | 100.00 | 58.10 | 100.00 | 58.10 | 100.00 |
| Std Deviation | 0.40 | 0.72 | 0.70 | 1.49 | 0.50 | 1.37 | 0.50 | 1.90 |

The particle size distribution is also determined for the particles entering the distributing device and the particles comprised in each respective exiting aperture. The hopper and the screw are part of the feeding device and these values represent the PSD of the entering SAP.

The PSD can be measured according to EDANA recommended Standard Test No. WSP 220.3.10 "Determination of the particle size distribution by sieve fractionation". According to EP 1 730 218 the logarithmic standard deviation of a PSD may be determined as follows: at first the particle size distribution is determined by sieving. The oversize percentages R at each particle size were plotted on a logarithmic scale. Logarithmic standard deviation ($\sigma\zeta$) is given as $\sigma\zeta = 0.5 \times \ln(X2/X1)$, wherein X1 and X2 are particle diameters for R=84.1% by weight and R=15.9% by weight.

| | Particles size | | | | | |
|---|---|---|---|---|---|---|
| | <45 μm | | 45-100 μm | | 100-200 μm | |
| | Std Dev | Average <45 μm | Std Dev | Average 45-100 μm | Std Dev | Average 100-200 μm |
| Hopper | 0.00 | 0.02 | 0.00 | 0.13 | 0.23 | 7.04 |
| Screw | 0.00 | 0.01 | 0.01 | 0.13 | 1.46 | 6.17 |
| Channel 1 | 0.00 | 0.00 | 0.01 | 0.16 | 0.08 | 5.75 |
| Channel 2 | 0.01 | 0.02 | 0.06 | 0.17 | 0.02 | 5.61 |
| Channel 3 | 0.03 | 0.02 | 0.10 | 0.20 | 0.16 | 7.22 |
| Channel 4 | 0.01 | 0.02 | 0.04 | 0.16 | 0.08 | 7.55 |

| 200-300 μm | | 300-400 μm | | 400-500 μm | | 500-600 μm | |
|---|---|---|---|---|---|---|---|
| Std Dev | Average 200-300 μm | Std Dev | Average 300-400 μm | Std Dev | Average 400-500 μm | Std Dev | Average 500-600 μm |
| 0.48 | 15.29 | 0.50 | 16.96 | 0.62 | 13.14 | 0.63 | 23.18 |
| 0.23 | 13.18 | 0.94 | 16.37 | 0.54 | 13.28 | 0.45 | 24.66 |
| 0.25 | 14.49 | 0.21 | 15.85 | 0.38 | 11.67 | 0.04 | 22.92 |
| 0.54 | 14.96 | 0.31 | 15.55 | 0.31 | 13.09 | 0.18 | 21.03 |
| 0.20 | 16.21 | 0.17 | 16.63 | 0.14 | 13.70 | 1.12 | 20.93 |
| 0.15 | 16.81 | 0.21 | 17.21 | 0.16 | 13.21 | 0.57 | 19.86 |

| 600-710 μm | | 710-850 μm | | >850 μm | |
|---|---|---|---|---|---|
| Std Dev | Average 600-710 μm | Std Dev | Average 710-850 μm | Std Dev | Average >850 μm |
| 0.38 | 20.04 | 0.36 | 4.15 | 0.00 | 0.07 |
| 0.01 | 22.11 | 0.20 | 4.05 | 0.00 | 0.07 |

-continued

| \multicolumn{6}{c}{Particles size} |
|---|---|---|---|---|---|
| 0.14 | 23.45 | 0.07 | 5.71 | 0.00 | 0.02 |
| 0.50 | 24.47 | 0.15 | 5.09 | 0.03 | 0.03 |
| 0.18 | 20.01 | 0.80 | 5.05 | 0.03 | 0.04 |
| 0.18 | 20.40 | 0.09 | 4.79 | 0.01 | 0.03 |

The invention claimed is:

1. A process for dosing super absorbent polymer particles into a plurality of particles flows, comprising the steps of:
(i) providing super absorbent polymer particles;
(ii) imparting a rotation to said particles, said step (ii) being performed with a continuously rotating mobile (11) having a J shape derived from a parabola having its axis on a radius of said mobile at a distance of 65% to 90% from a center of said mobile (11) and/or with an angle formed by a J curve at a periphery of the mobile with an equator plane of said mobile (11) from 5° to 30°, wherein the rotating mobile (11) is provided into a housing (12); and
(iii) collecting separate flows of particles.

2. The process of claim 1, wherein a gap between a circumference of the mobile (11) and the housing (12) is present and is about 5 mm to 20 mm.

3. The process of claim 1, wherein the mobile (11) has a diameter from 50 to 250 mm, and/or wherein the housing (12) has an inner diameter of about 60 to 300 mm.

4. The process of claim 1, wherein the rotating speed of said mobile (11) is from 100 to 1000 rpm, and/or wherein the rotating speed of said mobile (11) is such that the particles will operate at least one revolution, and/or wherein the rotating speed of said mobile (11) is such that the particles will have a peripheral speed from 0.5 m/s to 8 m/s.

5. The process of claim 1, wherein the provision (i) of the particles comprises supplying the particles gravitationally or using a screw device, and/or the provision (i) of the particles comprises supplying the particles through a circular nozzle (15) placed around an axis of rotation.

6. The process of claim 5, wherein the circular nozzle (15) defines an aperture which is annular in shape and has a lumen from 5 mm to 20 mm, and/or wherein the circular nozzle (15) is placed at a distance of 2 mm to 17 mm above the point of junction between the shape and the axis of the mobile (11), and/or wherein the circular nozzle (15) comprises an inner shape of conical geometry, with an angle relative to vertical from 45° to 75°.

7. The process of claim 1, wherein the housing (12) comprises a bottom part having an inner shape with an angle relative to vertical from 70° to 85°.

8. The process of claim 1, wherein the step (iii) of collecting the separate flows of particles comprises collecting particles into equally distributed apertures (14a, 14b, 14c, 14d) and/or wherein the step (iii) of collecting is for collecting a number of separate flows of particles from 2 to 8.

9. The process of claim 2, wherein the gap is 10 mm to 15 mm.

10. The process of claim 1, wherein the rotating mobile has a center and a periphery, and wherein the J shape of the rotating mobile (11) is derived from a parabola having its axis on a radius of said mobile, at a distance of 65% to 90% from the center of the rotating mobile (11) or wherein the J shape of the rotating mobile (11) comprises an angle formed by the J curve at the periphery of the mobile with the equator plane of said mobile (11) from 7° to 25°.

11. The process according to claim 1, the housing (12) has an inner diameter of 160 mm to 200 mm and a rotating speed of 300 to 500 rpm.

* * * * *